United States Patent
Burrows et al.

(10) Patent No.: US 6,960,602 B2
(45) Date of Patent: Nov. 1, 2005

(54) PIPERIDINE DERIVATIVES AS MODULATORS OF CHEMOKINE RECEPTORS

(75) Inventors: Jeremy Burrows, Macclesfield (GB); John Cumming, Macclesfield (GB)

(73) Assignee: AstraZeneca AB, Södertälje (SE)

(*) Notice: Subject to any disclaimer, the term of this patent is extended or adjusted under 35 U.S.C. 154(b) by 0 days.

(21) Appl. No.: 10/472,350

(22) PCT Filed: Mar. 19, 2002

(86) PCT No.: PCT/SE02/00542

§ 371 (c)(1),
(2), (4) Date: Sep. 18, 2003

(87) PCT Pub. No.: WO02/076948

PCT Pub. Date: Oct. 3, 2002

(65) Prior Publication Data

US 2004/0110794 A1 Jun. 10, 2004

(30) Foreign Application Priority Data

Mar. 22, 2001 (GB) .............................. 0107228

(51) Int. Cl.$^7$ ................... A61K 31/4468; C07D 211/58
(52) U.S. Cl. ....................... 514/329; 546/224; 546/213; 514/326
(58) Field of Search ................... 514/329, 326; 546/224, 213

(56) References Cited

U.S. PATENT DOCUMENTS

| | | | |
|---|---|---|---|
| 3,203,992 A | 8/1965 | Kunz et al. |
| 3,577,432 A | 5/1971 | Helsley et al. |
| 3,755,584 A | 8/1973 | Plotnikoff et al. |
| 3,818,017 A | 6/1974 | Janssen et al. |
| 3,894,030 A | 7/1975 | Janssen et al. |
| 4,029,801 A | 6/1977 | Cavalla et al. |
| 4,105,666 A | 8/1978 | Ward |
| 4,105,771 A | 8/1978 | Archibald et al. |
| 4,166,119 A | 8/1979 | Effland et al. |
| 4,246,267 A | 1/1981 | Vincent et al. |
| 4,264,613 A | 4/1981 | Regnier et al. |
| 4,338,323 A | 7/1982 | Regnier et al. |
| 5,576,321 A | 11/1996 | Krushinski, Jr. et al. |
| 5,614,523 A | 3/1997 | Audia et al. |
| 5,614,533 A | 3/1997 | Anderson et al. |
| 5,627,196 A | 5/1997 | Audia et al. |
| 5,688,960 A | 11/1997 | Shankar |
| 5,696,267 A | 12/1997 | Reichard et al. |
| 5,741,789 A | 4/1998 | Hibschman et al. |
| 5,789,402 A | 8/1998 | Audia et al. |
| 5,840,725 A | 11/1998 | Reichard et al. |

FOREIGN PATENT DOCUMENTS

| | | |
|---|---|---|
| DE | 37 23 568 A1 | 1/1989 |
| DE | 197 03 131 A1 | 7/1998 |
| DE | 197 55 268 A1 | 6/1999 |
| EP | 0 095 454 | 11/1983 |
| EP | 0 128 007 | 12/1984 |
| EP | 0 354 568 A2 | 2/1990 |
| EP | 0 407 217 A1 | 1/1991 |
| EP | 0 445 862 B1 | 9/1991 |
| EP | 0 457 686 B1 | 11/1991 |
| EP | 0 496 691 A1 | 7/1992 |
| EP | 0 587 311 A1 | 3/1994 |
| EP | 0 625 507 B1 | 11/1994 |
| EP | 0 643 057 A1 | 3/1995 |
| EP | 0 722 941 A2 | 7/1996 |
| EP | 0 903 349 A2 | 5/1999 |
| EP | 1 013 276 A1 | 6/2000 |
| FR | 2 190 430 | 2/1974 |
| GB | 1 368 012 | 9/1974 |
| GB | 1 404 868 | 9/1975 |
| GB | 1 425 354 | 2/1976 |
| GB | 1 532 671 | 11/1978 |
| GB | 1 538 542 | 1/1979 |
| GB | 1 544 191 | 4/1979 |
| JP | 63-264525 | 11/1988 |
| JP | 10259176 | 9/1998 |
| WO | WO 92/15579 | 9/1992 |
| WO | WO 93/13083 | 7/1993 |
| WO | WO 93/25528 | 12/1993 |
| WO | WO 94/27967 | 12/1994 |
| WO | WO 95/11880 | 5/1995 |
| WO | WO 96/26205 | 8/1996 |
| WO | WO 96/34857 | 11/1996 |
| WO | WO 96/39386 | 12/1996 |
| WO | WO 97/10207 | 3/1997 |

(Continued)

OTHER PUBLICATIONS

Mensonides–Harsema et al., "Synthesis and in Vitro and in Vivo Functional Studies of Ortho–Substituted Phenylpiperazine and N–Substituted 4–N–(o–Methoxyphenyl)aminopiperidine Analogues of WAY100635," J. Med. Chem., vol. 43, pp. 432–439 (2000).

Archibald et al., "Antihypertensive Ureidopiperidines", *J. Med. Chem.* 23:857–861 (1980).

Archibald et al., "Antiinflammatory 4–acylaminopiperidines", CAPLUS 77:34355 (1972).

(Continued)

*Primary Examiner*—Charanjit S. Aulakh
(74) *Attorney, Agent, or Firm*—Fish & Richardson P.C.

(57) ABSTRACT

The invention provides a compound of formula (I): wherein $R^1$, $R^2$, $R^3$, $R^{3a}$, $R^4$, $R^{4a}$, $R^5$, and $R^6$ are as defined; or a pharmaceutically acceptable salt thereof or a solvate thereof; compositions containing these compounds, processes for preparing them and their use as modulators of chemokine activity (especially CCR5 activity)

(I)

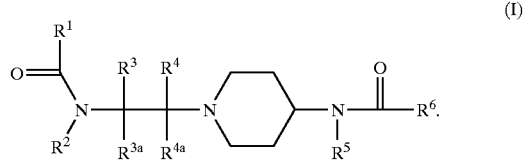

10 Claims, No Drawings

FOREIGN PATENT DOCUMENTS

| WO | WO 99/64394 | 12/1999 |
|---|---|---|
| WO | WO 99/65895 | 12/1999 |
| WO | WO 00/08013 | 2/2000 |
| WO | WO 00/21948 | 4/2000 |
| WO | WO 00/21952 | 4/2000 |
| WO | WO 00/23076 | 4/2000 |
| WO | WO 00/35449 | 6/2000 |
| WO | WO 00/35451 | 6/2000 |
| WO | WO 00/39108 | 7/2000 |
| WO | WO 00/53600 | 9/2000 |
| WO | WO 00/58305 | 10/2000 |
| WO | WO 00/61559 | 10/2000 |
| WO | WO 00/69820 | 11/2000 |
| WO | WO 00/76513 A1 | 12/2000 |
| WO | WO 00/76973 A1 | 12/2000 |
| WO | WO 01/14333 | 3/2001 |
| WO | WO 01/43744 | 6/2001 |
| WO | WO 01/44227 | 6/2001 |
| WO | WO 01/87839 A1 | 11/2001 |
| WO | WO 01/87839 | 11/2001 |
| WO | WO 01/92227 A1 | 12/2001 |
| WO | WO 02/066460 | 8/2002 |
| WO | WO 02/070479 | 9/2002 |
| WO | WO 02/076948 A1 | 10/2002 |
| WO | WO 02/079256 | 10/2002 |
| WO | WO 03/042177 | 5/2003 |
| WO | WO 03/042178 | 5/2003 |
| WO | WO 03/042205 | 5/2003 |

OTHER PUBLICATIONS

Caplus accession No. 1978:22640, document No. 88:22640, Yoshitomi Pharmaceutical Industries Ltd.: "Urea and thiourea derivatives" & JP, A2, 52085174, 19770715.

Caplus, accession No. 1990:558675, document No. 113:158675, Yoshitomi Pharmaceutical Industries, Ltd.: "Dihydroxycinnamic acid amide derivatives and their pharmaceutical compositions for enhancement of nerve growth factor (NGF) production" & JP, A2, 02104568, 19900417.

Cattanach et al., "Studies in the Indole Series. Part IV. Tetrahydro–1H–pyrido[4, 3–b]–indoles as Serotonin Antagonists", *J. Chem. Soc.* (C) 10:1235–1243 (1968).

Cohen et al., "Cytokine function: A study in biologic diversity", Caplus 125:31527 (1996).

Derwent Abstract 2000–587420/55, (2003), corresponding to Foreign Patent Document WO 00/53600, published Sep. 14, 2000 (Reference AYYY above).

Derwent Abstract 54050W/33 corresponding to Belgium Application BE 826994.

Derwent Abstract 93–339628/29 corresponding to PCT Application WO 00/23437 A1.

Derwent Abstract 96–136185/14 corresponding to Japanese Patent Application JP 08026999.

Derwent Abstract 96–136186/14 corresponding to Japanese Patent Application JP 08027000–A.

Derwent Abstract 96–136187/14 corresponding to Japanese Patent Application JP 08027001–A.

Derwent Abstract 97–212513/19, (2003), corresponding to Foreign Patent Document WO 97/10207 A1, published Mar. 20, 1997 (Reference AWW above).

Derwent Abstract 98–351249/49, (2003), corresponding to Foreign Patent Document JP 63–264525, published Nov. 1, 1988 (Reference AOO above).

Derwent Abstract 99–040684/04 corresponding to Japanese Patent Application JP 10298180–A/2.

Emonds–Alt et al., "Pharmacological Profile and Chemical Synthesis of SR 48968, a Non–Peptide Antagonist of the Neurokinin A ($NK_2$) Receptor", *Bioorganic & Medicinal Chemistry Letters* 3(5):925–930 (1993).

Friebe et al., "Piperidinopropyl derivatives and pharmaceutical compositions containing them", CAPLUS 94:103172 (1981).

Gerard, "Chemokine Receptors and Ligand Specificity: Understanding the Enigma", *Chemokines and Cancer* vol. 13, No. 72 (C–570):21–31, Feb. 17, 1999.

Granata et al., "Secretory phospholipases a(2) as multivalent mediators of inflammatory and allergic disorders", PubMed Abstract 12876405, also cited as *Int Arch Allergy Immunol.* 131(3):153–163 (2003).

Hesselgesser et al., "Identification and Characterization of Small Molecule Functional Antagonists of the CCR1 Chemokine Receptor", *J. Biol. Chem.* 273(25):15687–15692 (1998).

Howard et al., "Chemokines: progress toward identifying molecular targets for therapeutic agents", *Trends in Biotechnology* 14:46–51 (1996).

Janda, "A Soluble Polmer Approach to the "Fishing Out" Principle: Synthesis and Purification of β–Amino Alcohols", *J. Org. Chem.* 63:889–894 (1998).

Komai et al., "Structure–Activity Relationships of HIV–1 PR Inhibitors Containing AHPBA–II. Modification of Pryrrolidine Ring at P1'Proline", *Bioorganic & Medicinal Chemistry* 4(8):1365–1377 (1996).

Lawrence et al., "Automated Synthesis and Purification of Amides: Exploitation of Automated Solid Phase Extraction in Organic Synthesis", *Synthesis* 553–558, see table 1 (May 1997).

Leclerc et al., "Derivatives Related to Betaxolol with α–and β–Adrenergic Activities", *Arzneim.–Forsch./Drug. Res.* 35(11):1357–1367 (1985).

Meurer et al., "Discovery of potent human CCR5 antagonists for the treatment of HIV–I infection–II.", CAPLUS 2000:331722 (2000).

Navas III et al., "The Design and Synthesis of a Hapten for 1192U90, A Potential Atypical Antipsychotic Agent", *Synthetic Communications* 26(7):1411–1421 (1996).

Naya et al., "Design, Synthesis, and Discovery of a Novel CCR1 Antagonist", *J. Med. Chem.* 44:1429–1435 (2001).

Ng et al., "Discovery of Novel Non–Peptide CCR1 Receptor Antagonists", *Journal of Medicinal Chemistry* 42:4680–4694 (1999).

Payard et al., "N–Aminomethylated Derivatives of Some Hydroxamic Acids as Anti–Inflammatories", *Eur. J. Med. Chem.* pp. 1–10 (1975).

Rollins, "Chemokines", *Blood* 90(3):909–928 (1997).

Rubini et al., "Synthesis of Isosteric Methylene–Oxy Pseudodipeptide Analogues as Novel Amide Bond Surrogate Units", *Tetrahedron* 42(21):6039–6045 (1986).

Scott et al., "Secreted phospholipase A(2) enzymes as therapeutic targets", PubMed Abstract 12783578, also cited as *Expert Opin Ther Targets* 7(3):427–40 (2003).

Srulevitch et al., "4–Phenylamidopiperidines: synthesis, pharmacological testing and SAR analysis", *Acta Pharm. Jugosl.* 41:89–106 (1991).-

Srulevitch et al., "Design, Synthesis and SAR of Analgesics", QSAR: Quantitative Structure–Activity Relationships in Drug Design, pp. 377–381 (1989).

Stefano et al., "Human neutrophil and macrophage chemokinesis induced by cardiopulmonary bypass: Loss of DAME and IL–1 chemotaxis", *Journal of Neuroimmunology* 47:189–198 (1993).

Timmermans et al., "Hypotensive Properties of Benzodioxane Derivatives Structurally Related to R 28935. Comparison of Activity with some Receptor Affinities", *Arch. int. Pharmacodyn.* 255:321–334 (1982).

Wade et al., "Application of Base Cleavable Safety Catch Linkers to Solid Phase Library Production", *J. Comb. Chem.* 2:266–275, see p. 269 scheme 3 and table 4, compounds 32 a–m (2000).

Wright et al., "Discovery of Selective Dopamine D4 Receptor Antagonists: 1–Aryloxy–3–(4–Aryloxypiperidinyl)–2–Propanols", *Bioorganic & Medicinal Chemistry Letters* 7(11):1377–1380 (1997).

PIPERIDINE DERIVATIVES AS MODULATORS OF CHEMOKINE RECEPTORS

The present invention relates to heterocyclic derivatives having pharmaceutical activity, to processes for preparing such derivatives, to pharmaceutical compositions comprising such derivatives and to the use of such derivatives as active therapeutic agents.

Pharmaceutically active piperidine derivatives are disclosed in EP-A1-1013276, WO00/08013, WO99/38514 and WO99/04794.

Chemokines are chemotactic cytokines that are released by a wide variety of cells to attract macrophages, T cells, eosinophils, basophils and neutrophils to sites of inflammation and also play a rôle in the maturation of cells of the immune system. Chemokines play an important role in immune and inflammatory responses in various diseases and disorders, including asthma and allergic diseases, as well as autoimmune pathologies such as rheumatoid arthritis and atherosclerosis. These small, secreted molecules are a growing superfamily of 8–14 kDa proteins characterised by a conserved four cysteine motif. The chemokine superfamily can be divided into two main groups exhibiting characteristic structural motifs, the Cys-X-Cys (C—X—C, or α) and Cys-Cys (C—C, or β) families. These are distinguished on the basis of a single amino acid insertion between the NH-proximal pair of cysteine residues and sequence similarity.

The C—X—C chemokines include several potent chemoattractants and activators of neutrophils such as interleukin-8 (IL-8) and neutrophil-activating peptide 2 (NAP-2).

The C—C chemokines include potent chemoattractants of monocytes and lymphocytes but not neutrophils such as human monocyte chemotactic proteins 1–3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3 and CXCR4. These receptors represent good targets for drug development since agents that modulate these receptors would be useful in the treatment of disorders and diseases such as those mentioned above.

The CCR5 receptor is expressed on T-lymphocytes, monocytes, macrophages, dendritic cells, microglia and other cell types. These detect and respond to several chemokines, principally "regulated on activation normal T-cell expressed and secreted" (RANTES), macrophage inflammatory proteins (MIP) MIP-1a and MIP-1b and monocyte chemoattractant protein-2 (MCP-2).

This results in the recruitment of cells of the immune system to sites of disease. In many diseases it is the cells expressing CCR5 that contribute, directly or indirectly, to tissue damage. Consequently, inhibiting the recruitment of these cells is beneficial in a wide range of diseases.

CCR5 is also a co-receptor for HIV-1 and other viruses, allowing these viruses to enter cells. Blocking the receptor with a CCR5 antagonist or inducing receptor internalisation with a CCR5 agonist protects cells from viral infection.

The present invention provides a compound of formula (I):

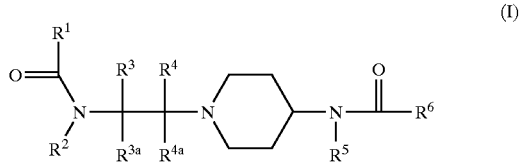

wherein:
$R^1$ is $C_{3-7}$ cycloalkyl, $C_{5-7}$ cycloalkenyl, heterocyclyl (itself optionally substituted by $C_{1-4}$ alkyl), $C_{1-8}$ alkyl (optionally substituted by $C_{3-6}$ cycloalkyl, $C_{5-6}$ cycloalkenyl, phenyl, heteroaryl, $S(O)_p R^7$, $CO_2 R^8$), $C_{3-6}$ alkenyl (optionally substituted by phenyl, heteroaryl, $S(O)_q R^9$, $CO_2 R^{10}$) or $C_{3-8}$ alkynyl;

$R^2$ is phenyl, heteroaryl, phenyl($C_{1-4}$ alkyl) or heteroaryl ($C_{1-4}$ alkyl);

$R^3$, $R^{3a}$, $R^4$ and $R^{4a}$ are, independently, hydrogen or $C_{1-4}$ alkyl;

$R^5$ is hydrogen, $C_{1-4}$ alkyl (optionally substituted by halogen, hydroxy, $C_{1-4}$ alkoxy, $C_{3-7}$ cycloalkyl, SH, $C_{1-4}$ alkylthio, cyano or $S(O)_q(C_{1-4}$ alkyl)), $C_{3-4}$ alkenyl, $C_{3-4}$ alkynyl or $C_{3-7}$ cycloalkyl;

$R^6$ is phenyl, heteroaryl, phenylNH, heteroarylNH, phenyl($C_{1-2}$)alkyl, heteroaryl($C_{1-2}$)alkyl, phenyl($C_{1-2}$ alkyl)NH or heteroaryl($C_{1-2}$ alkyl)NH;

$R^7$ and $R^9$ are, independently, $C_{1-4}$ alkyl, or, when p or q is 0, $C_{1-4}$ acyl;

$R^8$ and $R^{10}$ are, independently, hydrogen or $C_{1-4}$ alkyl;

wherein the phenyl and heteroaryl rings of any of the foregoing are independently optionally substituted by halo, cyano, nitro, hydroxy, $C_{1-4}$ alkyl, $C_{1-4}$ alkoxy, $S(O)_m C_{1-4}$ alkyl, $S(O)_2 NR^{11} R^{12}$, $NHS(O)_2(C_{1-4}$ alkyl), $NH_2$, $NH(C_{1-4}$ alkyl), $N(C_{1-4}$ alkyl)$_2$, $NHC(O)NH_2$, $C(O)NH_2$, $C(O)NH(C_{1-4}$ alkyl), $NHC(O)(C_{1-4}$ alkyl), $CO_2H$, $CO_2(C_{1-4}$ alkyl), $C(O)(C_{1-4}$ alkyl), $CF_3$, $CHF_2$, $CH_2F$, $CH_2CF_3$ or $OCF_3$;

$R^{11}$ and $R^{12}$ are, independently, hydrogen or $C_{1-4}$ alkyl, or together with a nitrogen or oxygen atom, may join to form a 5- or 6-membered ring which is optionally substituted with $C_{1-4}$ alkyl, $C(O)H$ or $C(O)(C_{1-4}$ alkyl);

m, p and q are, independently, 0, 1 or 2;

or a pharmaceutically acceptable salt thereof or a solvate thereof.

Certain compounds of the present invention can exist in different isomeric forms (such as enantiomers, diastereomers, geometric isomers or tautomers). The present invention covers all such isomers and mixtures thereof in all proportions.

Suitable salts include acid addition salts such as a hydrochloride, hydrobromide, phosphate, acetate, fumarate, maleate, tartrate, citrate, oxalate, methanesulphonate or p-toluenesulphonate.

The compounds of the invention may exist as solvates (such as hydrates) and the present invention covers all such solvates.

Alkyl groups and moieties are straight or branched chain and are, for example, methyl, ethyl, n-propyl or iso-propyl.

Alkenyl and alkynyl groups and moieties are, for example, vinyl, allyl or propargyl.

Cycloalkyl is a mono-, bi- or tri-cyclic structure such as, for example, cyclopropyl, cyclopentyl, cyclohexyl or adamantyl.

Cycloalkenyl comprises 1 double bond and is, for example, cyclopentenyl or cyclohexenyl.

Acyl is, for example, carbonyl substituted by $C_{1-6}$ alkyl or optionally substituted phenyl.

Heterocyclyl is a non-aromatic 3, 4, 5 or 6 membered ring comprising at least one heteroatom selected from the group comprising nitrogen, oxygen and sulphur. Heterocyclyl is, for example, aziridinyl, azetidinyl, oxetanyl, piperidinyl, 4,5-dihydro-oxazolyl, 4,5-dihydroimidazolyl, morpholinyl, pyrrolidinyl, piperazinyl, tetrahydrofuryl, tetrahydropyranyl or tetrahydrothiopyranyl (wherein the sulphur is optionally substituted with 1 or 2 oxygen atoms).

Heteroaryl is an aromatic 5 or 6 membered ring comprising at least one heteroatom selected from the group comprising nitrogen, oxygen and sulphur. Heteroaryl is, for example, pyrrolyl, imidazolyl, pyrazolyl, 1,2,3-triazolyl, 1,2,4-triazolyl, oxazolyl, isoxazolyl, oxadiazolyl, thiazolyl, isothiazolyl, thiadiazolyl, pyridinyl, pyrimidinyl, pyrazinyl, pyridazinyl, thienyl, furyl, quinolinyl, isoquinolinyl, dihydroisoquinolinyl, quinazolinyl, quinoxalinyl, indolyl, isoindolyl, benzimidazolyl, benzo[b]furyl, benzo[b]thienyl, phthalazinyl, indanyl, benzthiazolyl or cinnolinyl.

Phenylalkyl is, for example, benzyl, 1-(phenyl)ethyl or 2-(phenyl)ethyl.

Heteroarylalkyl is, for example, pyridinylmethyl, pyrimidinylmethyl or 2-(pyridinyl)ethyl.

The group $S(O)_2NR^{11}R^{12}$ is, for example, $S(O)_2NH_2$, $S(O)_2NH(C_{1-4}$ alkyl), $S(O)_2N(C_{1-4}$ alkyl)$_2$, $S(O)_2(4$-C(O)H-piperazin-1-yl) or $S(O)_2(4$-C(O)CH$_3$-piperazin-1-yl).

Phenyl($C_{1-2}$ alkyl)NH is, for example, benzylamino. Heteroaryl($C_{1-2}$ alkyl)NH is, for example, pyridinylCH$_2$NH, pyrimidinylCH$_2$NH or pyridinylCH(CH$_3$)NH.

In one particular aspect $R^1$ is $C_{3-7}$ cycloalkyl. In another aspect $R^1$ is cyclopropyl or cyclobutyl.

In a further aspect $R^2$ is optionally substituted phenyl (especially optionally substituted by halo, cyano, methyl, ethyl, methoxy, ethoxy, $NH_2$, $NHCH_3$, $N(CH_3)_2$, $CF_3$, $CHF_2$, $CH_2F$, $CH_2CF_3$ or $OCF_3$). In another aspect $R^2$ is optionally substituted phenyl (especially optionally substituted by halogen or $CF_3$). Halogen is especially chlorine or fluorine. It is especially preferred that phenyl is ortho- or meta-substituted. For example $R^2$ is unsubstituted phenyl, 3-fluorophenyl, 3-chlorophenyl, 4-fluorophenyl or 4-$CF_3$-phenyl.

In a still further aspect $R^3$ and $R^{3a}$ are both hydrogen.

In yet another aspect $R^4$ and $R^{4a}$ are hydrogen or methyl.

In another aspect $R^4$ is hydrogen or methyl and $R^{4a}$ is hydrogen.

In a further aspect $R^4$ and $R^{4a}$ are hydrogen or methyl, and $R^3$ and $R^{3a}$ are all hydrogen.

In a still further aspect $R^3$, $R^{3a}$, $R^4$ and $R^{4a}$ are all hydrogen.

In another aspect $R^5$ is hydrogen or $C_{1-4}$ alkyl (such as methyl, ethyl or iso-propyl), $C_{3-4}$ alkenyl (for example allyl), $C_{3-4}$ alkynyl (for example propargyl), $C_{3-7}$ cycloalkyl (for example cyclopropyl) or $C_{3-7}$ cycloalkyl($C_{1-4}$ alkyl) (for example cyclopropylCH$_2$).

In yet another aspect of the invention $R^5$ is methyl, ethyl, allyl or cyclopropyl.

In a still further aspect $R^6$ is preferably optionally substituted benzyl, especially benzyl singly substituted (such as in the 4-position) by $S(O)_2(C_{1-4})$alkyl (such as $S(O)_2CH_3$) or $S(O)_2NR^9R^{10}$ {$R^9$ and $R^{10}$ are, independently, hydrogen or $C_{1-4}$ alkyl, or together with a nitrogen or oxygen atom, may join to form a 5- or 6-membered ring which is optionally substituted with $C_{1-4}$ alkyl, C(O)H or C(O)($C_{1-4}$ alkyl)} (such as $S(O)_2NH_2$, $S(O)_2NH(CH_3)$, $S(O)_2N(CH_3)_2$, $S(O)_2$(4-C(O)H-piperazin-1-yl) or $S(O)_2$(4-C(O)CH$_3$-piperazin-1-yl). The variables $R^9$ and $R^{10}$ are especially hydrogen.

In yet another aspect $R^6$ is optionally substituted benzyl, especially benzyl singly substituted (such as in the 4-position) by halo (such as fluoro), $S(O)_2(C_{1-4})$alkyl (such as $S(O)_2CH_3$) or $S(O)_2NH_2$.

In a further aspect $R^6$ is optionally substituted benzyl, especially benzyl singly substituted (such as in the 4-position) by halo (such as fluoro) or $S(O)_2(C_{1-4})$alkyl (such as $S(O)_2CH_3$).

In one aspect the present invention provides a compound of formula (Ia):

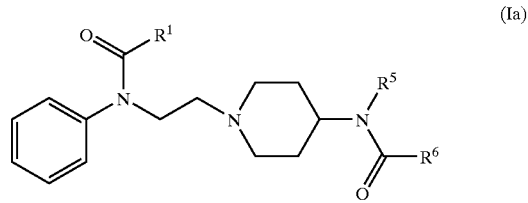

(Ia)

wherein $R^1$, $R^5$ and $R^6$ are as hereinbefore defined.

The following compounds illustrate the invention.

TABLE I

All compounds in Table I are of formula (Ia) below.

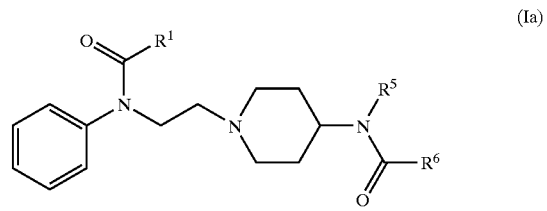

(Ia)

| Compound No. | $R^1$ | $R^5$ | $R^6$ | LCMS (MH+) |
|---|---|---|---|---|
| 1 | Cyclobutyl | Me | CH$_2$Ph-4-F | 452 |
| 2 | Cyclobutyl | Et | CH$_2$Ph-4-F | 466 |
| 3 | Cyclopropyl | Me | CH$_2$Ph-4-F | 438 |
| 4 | CH$_2$-2-Thiophene | Et | CH$_2$Ph-4-S(O)$_2$Me | 568 |
| 5 | C(=CH$_2$)CH$_2$CO$_2$Me | Et | CH$_2$Ph-4-S(O)$_2$Me | 570 |
| 6 | CH(Me)CH$_2$SAc—(R) | Et | CH$_2$Ph-4-S(O)$_2$Me | 588 |
| 7 | CH$_2$S(O)$_2$Me | Et | CH$_2$Ph-4-S(O)$_2$Me | 562 (M − H)+ |
| 8 | Cyclopropyl | Et | CH$_2$Ph-4-F | |
| 9 | Cyclopropyl | Et | CH$_2$Ph-4-S(O)$_2$Me | |
| 10 | Cyclopropyl | Et | CH$_2$Ph-4-S(O)$_2$Me | |
| 11 | Cyclobutyl | Et | CH$_2$Ph-4-S(O)$_2$NH$_2$ | |
| 12 | Cyclopropyl | Et | CH$_2$Ph-4-S(O)$_2$NH$_2$ | |
| 13 | Cyclobutyl | allyl | CH$_2$Ph-4-S(O)$_2$Me | |
| 14 | Cyclopropyl | allyl | CH$_2$Ph-4-S(O)$_2$Me | |
| 15 | Cyclobutyl | allyl | CH$_2$Ph-4-S(O)$_2$NH$_2$ | |
| 16 | Cyclopropyl | allyl | CH$_2$Ph-4-S(O)$_2$NH$_2$ | |
| 17 | Cyclobutyl | Cyclopropyl | CH$_2$Ph-4-S(O)$_2$Me | |
| 18 | Cyclopropyl | Cyclopropyl | CH$_2$Ph-4-S(O)$_2$Me | |
| 19 | Cyclobutyl | Cyclopropyl | CH$_2$Ph-4-S(O)$_2$NH$_2$ | |
| 20 | Cyclopropyl | Cyclopropyl | CH$_2$Ph-4-S(O)$_2$NH$_2$ | |

The compounds of formula (I) and (Ia) can be prepared as shown in Schemes 1 and 2 below.

A compound of formula (I) or (Ia) can be prepared by reacting a compound of formula (II):

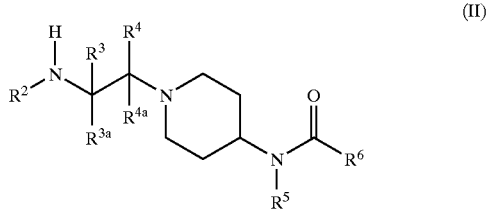

(II)

with either an acid halide of formula R¹C(O)Cl in a suitable solvent (such as a chlorinated solvent, for example CH₂Cl₂), or an acid of formula R¹CO₂H in the presence of a suitable coupling agent and in a suitable solvent. Suitable coupling agents include PyBrOP™ (bromo-tris-pyrrolidino-phosphonium hexafluorophosphate), HATU (O-(7-azabenzotriazol-1-yl)-N,N,N',N'-tetramethyluronium hexafluorophosphate), HBTU (O-benzotriazol-1-yl-N,N,N',N'-tetramethyluronium hexafluorophosphate), EDCI (ethyl dimethylaminopropyl carbodiimide hydrochloride), HOBT (1-hydroxybenzotriazole), and DMAP (N,N-dimethylaminopyridine).

In a further aspect the invention provides processes for preparing the compounds of formula (I) or (Ia). Many of the intermediates in the processes shown in Schemes 1 and 2 are novel and these are provided as further features of the invention.

The compounds of the invention have activity as pharmaceuticals, in particular as modulators (such as agonists, partial agonists, inverse agonists or antagonists) of chemokine receptor (especially CCR5) activity, and may be used in the treatment of autoimmune, inflammatory, proliferative or hyperproliferative diseases, or immunologically-mediated diseases (including rejection of transplanted organs or tissues and Acquired Immunodeficiency Syndrome (AIDS)). Examples of these conditions are:

(1) (the respiratory tract) obstructive diseases of airways including: chronic obstructive pulmonary disease (COPD) (such as irreversible COPD); pulmonary fibrosis; asthma {such as bronchial, allergic, intrinsic, extrinsic or dust asthma, particularly chronic or inveterate asthma (for example late asthma or airways hyper-responsiveness)}; bronchitis {such as eosinophilic bronchitis}; acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofoulous rhinitis; seasonal rhinitis including rhinitis nervosa (hay fever) or vasomotor rhinitis; sarcoidosis; farmer's lung and related diseases; nasal polyposis; fibroid lung or idiopathic interstitial pneumonia;

(2) (bone and joints) arthrides including rheumatic, infectious, autoimmune, seronegative spondyloarthropathies (such as ankylosing spondylitis, psoriatic arthritis or Reiter's disease), Behcet's disease, Sjogren's syndrome or systemic sclerosis;

(3) (skin and eyes) psoriasis, atopic dermatitis, contact dermatitis or other eczmatous dermitides, seborrhoetic dermatitis, lichen planus, phemphigus, bullous phemphigus, epidermolysis bullosa, urticaria, angiodermas, vasculitides erythemas, cutaneous eosinophilias, uveitis, alopecia areata or vernal conjunctivitis;

(4) (gastrointestinal tract) Coeliac disease, proctitis, eosinophilic gastro-enteritis, mastocytosis, Crohn's disease, ulcerative colitis, irritable bowel disease or food-related allergies which have effects remote from the gut (for example migraine, rhinitis or eczema);

(5) (Allograft rejection) acute and chronic following, for example, transplantation of kidney, heart, liver, lung, bone marrow, skin or cornea; or chronic graft versus host disease; and/or (6) (other tissues or diseases) Alzheimer's disease, multiple sclerosis, atherosclerosis, inhibiting the entry of viruses into target cells, Acquired Immunodeficiency Syndrome (AIDS), lupus disorders (such as lupus erythematosus or systemic lupus), erythematosus, Hashimoto's thyroiditis, myasthenia gravis, type I diabetes, nephrotic syndrome, eosinophilia fascitis, hyper IgE syndrome, leprosy (such as lepromatous leprosy), peridontal disease, sezary syndrome, idiopathic thrombocytopenia pupura, disorders of the menstrual cycle, glomerulonephritis or cerebral malaria.

The compounds of the present invention are also of value in inhibiting the entry of viruses (such as human immunodeficiency virus (HIV)) into target calls and, therefore, are of value in the prevention of infection by viruses (such as HIV), the treatment of infection by viruses (such as HIV) and the prevention and/or treatment of acquired immune deficiency syndrome (ADS).

According to a further feature of the invention there is provided a compound of the formula (I) or (Ia), or a pharmaceutically acceptable salt thereof or a solvate thereof, for use in a method of treatment of a warm blooded animal (such as man) by therapy (including prophylaxis).

According to a further feature of the present invention there is provided a method for modulating chemokine receptor activity (especially CCR5 receptor activity) in a warm blooded animal, such as man, in need of such treatment, which comprises administering to said animal an effective amount of a compound of the present invention, or a pharmaceutically acceptable salt thereof or a solvate thereof.

The present invention further provides a method of treating a chemokine mediated disease state (especially a CCR5 mediated disease state, such as rheumatoid arthritis) in a warm blooded animal (such as man) suffering from, or at risk of, said disease, which comprises administering to an animal in need of such treatment a therapeutically effective amount of a compound of formula (I) or (Ia), or a pharmaceutically acceptable salt thereof or solvate thereof.

The present invention also provides the use of a compound of the invention, or a pharmaceutically acceptable salt thereof or a solvate thereof, as a medicament, especially a medicament for the treatment of transplant rejection, respiratory disease, psoriasis or arthritis (especially rheumatoid arthritis). [Respiratory disease is, for example, COPD, asthma {such as bronchial, allergic, intrinsic, extrinsic or dust asthma, particularly chronic or inveterate asthma (for example late asthma or airways hyper-responsiveness)} or rhinitis {acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofoulous rhinitis; seasonal rhinitis including rhinitis nervosa (hay fever) or vasomotor rhinitis}; and is particularly asthma or rhinitis].

The invention also provides a compound of the formula (I) or (Ia), or a pharmaceutically acceptable salt thereof or a solvate thereof, for use as a medicament, especially a medicament for the treatment of transplant rejection, respiratory disease, psoriasis or arthritis (especially rheumatoid arthritis).

The invention also provides a compound of the formula (I) or (Ia), or a pharmaceutically acceptable salt thereof or a solvate thereof, for use in therapy (including prophylaxis); for example in the treatment of a chemokine mediated disease state (especially a CCR5 mediated disease state) in a warm blooded animal, such as man, such as in the treatment of rheumatoid arthritis.

The invention also provides a compound of the formula (I) or (Ia), or a pharmaceutically acceptable salt thereof or a solvate thereof, for use as a medicament, especially a medicament for the treatment of rheumatoid arthritis.

In another aspect the present invention provides the use of a compound of the formula (I) or (Ia), or a pharmaceutically acceptable salt thereof or a solvate thereof, in the manufacture of a medicament for use in therapy (for example in modulating chemokine receptor activity (especially CCR5 receptor activity (especially in the treatment of rheumatoid arthritis)) in a warm blooded animal, such as man).

The invention further provides the use of a compound of formula (I) or (Ia), or a pharmaceutically acceptable salt thereof, in the manufacture of a medicament for use in the treatment of:

(1) (the respiratory tract) obstructive diseases of airways including: chronic obstructive pulmonary disease (COPD) (such as irreversible COPD); asthma {such as bronchial, allergic, intrinsic, extrinsic or dust asthma, particularly chronic or inveterate asthma (for example late asthma or airways hyper-responsiveness)}; bronchitis {such as eosinophilic bronchitis}; acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofoulous rhinitis; seasonal rhinitis including rhinitis nervosa (hay fever) or vasomotor rhinitis; sarcoidosis; farmer's lung and related diseases; nasal polyposis; fibroid lung or idiopathic interstitial pneumonia;

(2) (bone and joints) arthrides including rheumatic, infectious, autoimmune, seronegative spondyloarthropathies (such as ankylosing spondylitis, psoriatic arthritis or Reiter's disease), Behcet's disease, Sjogren's syndrome or systemic sclerosis;

(3) (skin and eyes) psoriasis, atopic dermatitis, contact dermatitis or other eczmatous dermitides, seborrhoetic dermatitis, lichen planus, phemphigus, bullous phemphigus, epidermolysis bullosa, urticaria, angiodermas, vasculitides erythemas, cutaneous eosinophilias, uveitis, alopecia areata or vernal conjunctivitis;

(4) (gastrointestinal tract) Coeliac disease, proctitis, eosinophilic gastro-enteritis, mastocytosis, Crohn's disease, ulcerative colitis, irritable bowel disease or food-related allergies which have effects remote from the gut (for example migraine, rhinitis or eczema);

(5) (Allograft rejection) acute and chronic following, for example, transplantation of kidney, heart, liver, lung, bone marrow, skin or cornea; or chronic graft versus host disease; and/or (6) (other tissues or diseases) Alzheimer's disease, multiple sclerosis, atherosclerosis, Acquired Immunodeficiency Syndrome (AIDS), lupus disorders (such as lupus erythematosus or systemic lupus), erythematosus, Hashimoto's thyroiditis, myasthenia gravis, type I diabetes, nephrotic syndrome, eosinophilia fascitis, hyper IgE syndrome, leprosy (such as lepromatous leprosy), peridontal disease, sezary syndrome, idiopathic thrombocytopenia pupura or disorders of the menstrual cycle;

in a warm blooded animal, such as man.

In order to use a compound of the invention, or a pharmaceutically acceptable salt thereof or solvate thereof, for the therapeutic treatment of a warm blooded animal, such as man, in particular modulating chemokine receptor (for example CCR5 receptor) activity, said ingredient is normally formulated in accordance with standard pharmaceutical practice as a pharmaceutical composition.

Therefore in another aspect the present invention provides a pharmaceutical composition which comprises a compound of the formula (I) or (Ia), or a pharmaceutically acceptable salt thereof or a solvate thereof (active ingredient), and a pharmaceutically acceptable adjuvant, diluent or carrier. In a further aspect the present invention provides a process for the preparation of said composition which comprises mixing active ingredient with a pharmaceutically acceptable adjuvant, diluent or carrier. Depending on the mode of administration, the pharmaceutical composition will preferably comprise from 0.05 to 99% w (per cent by weight), more preferably from 0.05 to 80% w, still more preferably from 0.10 to 70% w, and even more preferably from 0.10 to 50% w, of active ingredient, all percentages by weight being based on total composition.

The pharmaceutical compositions of this invention may be administered in standard manner for the disease condition that it is desired to treat, for example by topical (such as to the lung and/or airways or to the skin), oral, rectal or parenteral administration. For these purposes the compounds of this invention may be formulated by means known in the art into the form of, for example, aerosols, dry powder formulations, tablets, capsules, syrups, powders, granules, aqueous or oily solutions or suspensions, (lipid) emulsions, dispersible powders, suppositories, ointments, creams, drops and sterile injectable aqueous or oily solutions or suspensions.

A suitable pharmaceutical composition of this invention is one suitable for oral administration in unit dosage form, for example a tablet or capsule which contains between 0.1 mg and 1 g of active ingredient.

In another aspect a pharmaceutical composition of the invention is one suitable for intravenous, subcutaneous or intramuscular injection.

Each patient may receive, for example, an intravenous, subcutaneous or intramuscular dose of 0.01 $mgkg^{-1}$ to 100 $mgkg^{-1}$ of the compound, preferably in the range of 0.1 $mgkg^{-1}$ to 20 $mgkg^{-1}$ of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose, the composition being administered 1 to 4 times per day.

The following illustrate representative pharmaceutical dosage forms containing the compound of formula (I) or (Ia), or a pharmaceutically acceptable salt thereof or a solvent thereof (hereafter Compound X), for therapeutic or prophylactic use in humans:

(a)

| Tablet I | mg/tablet |
| --- | --- |
| Compound X | 100 |
| Lactose Ph. Eur. | 179 |
| Croscarmellose sodium | 12.0 |
| Polyvinylpyrrolidone | 6 |
| Magnesium stearate | 3.0 |

(b)

| Tablet II | mg/tablet |
| --- | --- |
| Compound X | 50 |
| Lactose Ph. Eur. | 229 |
| Croscarmellose sodium | 12.0 |
| Polyvinylpyrrolidone | 6 |
| Magnesium stearate | 3.0 |

(c)

| Tablet III | mg/tablet |
| --- | --- |
| Compound X | 1.0 |
| Lactose Ph. Eur. | 92 |
| Croscarmellose sodium | 4.0 |
| Polyvinylpyrrolidone | 2.0 |
| Magnesium stearate | 1.0 |

(d)

| Capsule | mg/capsule |
| --- | --- |
| Compound X | 10 |
| Lactose Ph. Eur. | 389 |
| Croscarmellose sodium | 100 |
| Magnesium stearate | 1.0 |

(e)

| Injection I | (50 mg/ml) |
| --- | --- |
| Compound X | 5.0% w/v |
| Isotonic aqueous solution | to 100% |

Buffers, pharmaceutically-acceptable cosolvents such as polyethylene glycol, polypropylene glycol, glycerol or ethanol or complexing agents such as hydroxy-propyl β-cyclodextrin may be used to aid formulation.

The above formulations may be obtained by conventional procedures well known in the pharmaceutical art. The tablets (a)–(c) may be enteric coated by conventional means, for example to provide a coating of cellulose acetate phthalate.

The invention will now be illustrated by the following non-limiting examples in which, unless stated otherwise:

(i) temperatures are given in degrees Celsius (° C.); operations were carried out at room or ambient temperature, that is, at a temperature in the range of 18–25° C.;

(ii) organic solutions were dried over anhydrous magnesium sulphate; evaporation of solvent was carried out using a rotary evaporator under reduced pressure (600–4000 Pascals; 4.5–30 mm Hg) with a bath temperature of up to 60° C.;

(iii) chromatography unless otherwise stated means flash chromatography on silica gel; thin layer chromatography (TLC) was carried out on silica gel plates; where a "Bond Elut" column is referred to, this means a column containing 10 g or 20 g of silica of 40 micron particle size, the silica being contained in a 60 ml disposable syringe and supported by a porous disc, obtained from Varian, Harbor City, Calif., USA under the name "Mega Bond Elut SI". Where an "Isolute™ SCX column" is referred to, this means a column containing benzenesulphonic acid (non-endcapped) obtained from International Sorbent Technology Ltd., 1st House, Duffryn Industial Estate, Ystrad Mynach, Hengoed, Mid Clamorgan, UK. Where "Argonaut™ PS-tris-amine scavenger resin" is referred to, this means a tris-(2-aminoethyl)amine polystyrene resin obtained from Argonaut Technologies Inc., 887 Industrial Road, Suite G, San Carlos, Calif., USA.

(iv) in general, the course of reactions was followed by TLC and reaction times are given for illustration only;

(v) yields, when given, are for illustration only and are not necessarily those which can be obtained by diligent process development; preparations were repeated if more material was required;

(vi) when given, $^1$H NMR data is quoted and is in the form of delta values for major diagnostic protons, given in parts per million (ppm) relative to tetramethylsilane (TMS) as an internal standard, determined at 300 MHz using perdeuterio DMSO ($CD_3SOCD_3$) as the solvent unless otherwise stated; coupling constants (J) are given in Hz;

(vii) chemical symbols have their usual meanings; SI units and symbols are used;

(viii) solvent ratios are given in percentage by volume;

(ix) mass spectra (MS) were run with an electron energy of 70 electron volts in the chemical ionisation (APCI) mode using a direct exposure probe; where indicated ionisation was effected by electrospray (ES); where values for m/z are given, generally only ions which indicate the parent mass are reported, and unless otherwise stated the mass ion quoted is the positive mass ion–$(M+H)^+$;

(x) LCMS characterisation was performed using a pair of Gilson 306 pumps with Gilson 233 XL sampler and Waters ZMD4000 mass spectrometer. The LC comprised water symmetry 4.6×50 column C18 with 5 micron particle size. The eluents were: A, water with 0.05% formic acid and B, acetonitrile with 0.05% formic acid. The eluent gradient went from 95% A to 95% B in 6 minutes. Where indicated ionisation was effected by electrospray (ES); where values for m/z are given, generally only ions which indicate the parent mass are reported, and unless otherwise stated the mass ion quoted is the positive mass ion–$(M+H)^+$ and (xi) the following abbreviations are used:

| | |
| --- | --- |
| DMF | N,N-dimethylformamide; |
| THF | tetrahydrofuran; |
| DCM | dichloromethane; |
| HATU | O-(7-Azabenzotriazol-1-yl)-N,N,N',N'-tetramethyluronium hexafluorophosphate; |
| Boc | tert-butoxycarbonyl; and |
| MeOH | methanol. |

EXAMPLE 1

This Example illustrates the preparation of N-[1-(N-phenyl-N-cyclobutanecarbonyl-2-ethylamino)-4-piperidinyl]-N-methyl-4-fluorophenylacetamide (Compound No. 1 of Table I).

To a solution of cyclobutane carboxylic acid (50 mg, 0.5 mmol) in dichloromethane (DCM) (10 mL) was added oxalyl chloride (64 mg, 0.5 mmol) and the resulting mixture was stirred at room temperature for 5 h. The mixture was evaporated and the residue was dissolved in DCM (10 mL). N-[1-(N-Phenyl-2-ethylamino)-4-piperidinyl]-N-methyl-4-fluorophenylacetamide (150 mg, 0.43 mmol) was added followed by N,N-diisopropylethylamine (1.5 mmol). The resulting mixture was stirred at room temperature for 20 h, then partitioned between water and ethyl acetate. The organic phase was dried and evaporated. The crude product was purified by eluting through a 20 g Bond Elut cartridge with a gradient of 0–30% methanol in ethyl acetate yielding the title compound (67 mg); $^1$H NMR: δ 1.23 (br d, 1H), 1.36 (br d, 1H), 1.6 (m, 4H), 1.92 (m, 2H), 2.05 (m, 3H), 2.30 (m, 2H), 2.61 (s, 1H), 2.80 (s, 3H), 2.9–3.8 (m, 7H), 4.20 (m, 1H), 7.05 (m, 3H), 7.20 (d, 3H), 7.38 (m, 3H); MSS:452.

Compound No. 3 of Table I was prepared in a similar manner:

$^1$H NMR: δ0.61 (m, 2H), 0.76 (m, 2H), 1.30 (br dd, 2H), 1.50 (m, 2H), 1.90 (br q, 2H), 2.30 (br s, 2H), 2.60 (s, 1H), 2.80 (s, 3H), 3.2–3.8 (m, 6H), 4.18 (m 1H), 7.05 (m 3H), 7.20 (m 2H), 7.32 (d, 2H), 7.40 (m, 2H).

Methods

Starting materials are commercially available, have been described in the literature or can be prepared by adaptation of literature methods. Examples of literature methods include: P. Richter, Ch. Garbe and G. Wagner, *E. Ger. Pharmazie*, 1974, 29(4), 256–262; C. Oniscu, D. Nicoara and G. Funieru, "4-(Ureidosulfonyl)phenylacetic acid and its ureide", R079-966646, (Romanian document); and M. A. Zahran, M. M. Ali, Y. A. Mohammed and A. A. Shehata, *Int. J. Chem.*, 1993, 4(3), 61.

Method 1

N-[1-(N-Phenyl-2-ethylamino)-4-piperidinyl]-N-methyl-4-fluorophenylacetamide

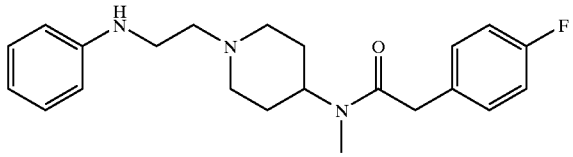

To a solution of 1-(N-phenyl-2-ethylamino)-4-methylaminopiperidine (466 mg, 2.0 mmol) in N,N-dimethylformamide (DMF) (10 mL) was added 4-fluorophenylacetic acid (323 mg, 2.1 mmol), HATU (800 mg, 2.1 mmol) and N,N-diisopropylethylamine (0.4 mL) and the resulting mixture was stirred at room temperature for 20 h. Water was added and the resulting mixture extracted with ethyl acetate. The organic extract was dried and evaporated affording the title compound (340 mg); $^1$H NMR: 1.40 (m, 2H), 1.70 (m, 2H), 2.65 (m, 2H), 2.80 (s, 3H), 2.9–3.2 (m, 5H), 3.70 (m, 3H), 4.23 (m 1H), 6.55 (m, 3H), 7.02 (m, 4H), 7.20 (m, 2H); MS: 370.

Method 2

1-(N-Phenyl-2-ethylamino)-4-methylaminopiperidine

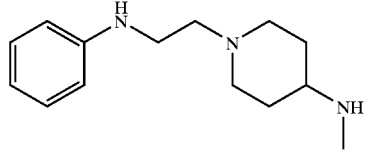

To a solution of 1-(2-anilinoacetyl)-4-Boc-aminopiperidine (3.33 g, 10.0 mmol) in THF (100 mL) was added lithium aluminium hydride (20 mL 1M in THF) and the resulting mixture stirred at reflux for 16 h. After cooling to room temperature the reaction was treated with 2M aqueous sodium hydroxide solution and the resulting mixture was filtered. The filtrate was evaporated then redissolved in ethyl acetate. This solution was washed with water, dried and evaporated giving the title compound as an oil (2.1 g); $^1$H NMR: 1.21 (dq, 2H), 1.75 (br d, 2H), 1.97 (dt, 2H0, 2.26 (m, 4H), 2.45 (t, 2H), 2.81 (br d, 2H), 3.07 (q, 2H), 5.27 (t, 1H), 6.49 (t, 1H), 6.55 (d, 2H), 7.04 (t, 2H); MS: 234.

Method 3

1-(2-Anilinoacetyl)-4-Boc-aminopiperidine

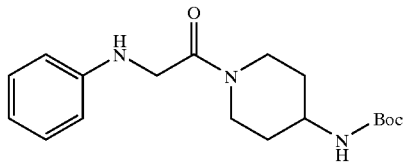

To a solution of 4-Boc-aminopiperidine (7.0 g, 35 mmol) in (DMF) (100 mL) was added 2-anilinoacetic acid (4.89 g, 33 mmol), HATU (13.3 g, 35 mmol) and N,N-diisopropylethylamine (6.1 mL) and the resulting mixture was stirred at room temperature for 20 h. Water was added and the resulting precipitate collected and dried affording the title compound as a solid (8.2 g, 74%); $^1$H NMR: 1.39 (s, 9H), 1.76 (br t, 2H), 2.75 (m, 1H), 3.04 (m, 1H), 3.5 (m, 3H), 3.84 (m, 3H), 4.20 (br d, 1H), 5.42 (t, 1H), 6.55 (t, 1H), 6.60 (d, 2H), 6.85 (m, 1H), 7.05 (t, 2H); MS: 278 (MH$^+$-2-butene).

Method 4

N-[1-(N-Phenyl-2-ethylamino)-4-piperidinyl]-N-ethyl-4-methanesulfonylphenylacetamide

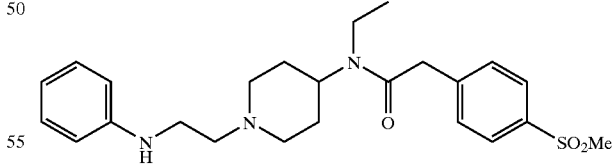

To a mixture of N-(4-piperidinyl)-N-ethyl-4-methanesulfonylphenylacetamide (2.0 g, 6.2 mmol) and N-(2-chloroethyl)aniline hydrochloride (1.2 g, 6.2 mmol) (J. Med. Chem. 1965, 173) in 4-methyl-2-pentanone (15 mL) was added potassium carbonate (2.56 g, 18.6 mmol) and potassium iodide (150 mg, 0.9 mmol) and the resulting mixture stirred at reflux for 20 h. After cooling to room temperature the solid was removed by filtration and the filtrate concentrated. The residue was purified by Bond Elut chromatography (eluent 5% MeOH/DCM) to afford, after trituration with diethyl ether, the title compound as a white solid (1.30 g, 50%); ¹H NMR (d6 DMSO, 373K): 1.1 (t, 3H), 1.4 (m, 2H), 1.8 (m, 2H), 2.1 (m, 2H), 2.5 (m, 2H), 3.1 (m, 5H), 3.3 (q, 2H), 3.8 (s, 2H), 5.0 (m, 1H), 6.6 (m, 3H), 7.1 (dd, 2H), 7.5 (d, 2H), 7.8 (d, 2H); MS: 444.

Method 5

N-(4-Piperidinyl)-N-ethyl-4-methanesulfonylphenylacetamide

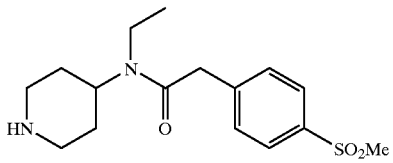

To a solution of N-(1-phenylmethyl-4-piperidinyl)-N-ethyl-4-methanesulfonylphenyl-acetamide (34 g, 82 mmol) in ethanol (600 ml) was added ammonium formate (40 g). The mixture was purged with argon and 30% Pd on carbon (4.2 g) was added. The resulting mixture was stirred at reflux for 4 h, then allowed to cool and filtered through diatomaceous earth. The filtrate was evaporated to give a thick oil which solidified on standing to yield the title compound (24.9 g. 77 mmol); ¹H NMR: 1.02 and 1.15 (t, 3H), 1.4 –1.6 (br m, 4H), 2.45 (m, 2H), 2.93 (br m, 2H), 3.18 (s, 3H), 3.20 and 3.32 (q, 2H), 3.72 and 4.18 (m, 1H), 3.80 and 3.87 (s, 2H), 7.50 (m, 2H), 7.85 (m, 2H); MS: 325.

Method 6

N-(1-Phenylmethyl-4-piperidinyl)-N-ethyl-4-methanesulfonylphenylacetamide

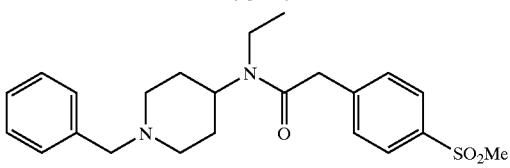

To a solution of 1-phenylmethyl-4-ethylaminopiperidine dihydrochloride (32.0 g, 110 mmol) in DCM (500 mL) was added N,N-diisopropylethylamine (60 mL) with stirring to ensure complete dissolution. 4-Methanesulfonylphenylacetic acid (25.0 g, 117 mmol), 4-dimethylaminopyridine (2.0 g) and dicyclohexylcarbodiimide (25.0 g, 121 mmol) were added and the resulting mixture was stirred at room temperature for 20 h. The precipitate was removed by filtration and the resulting solution was washed successively with 2N aqueous HCl, water and 1N aqueous NaOH, dried (MgSO₄) and evaporated. The residue was purified by silica gel chromatography (eluent 10% MeOH/ethyl acetate) to afford the title compound (35 g, 76%); ¹H NMR: 1.00 and 1.14 (t, 3H), 1.45 and 1.70 (m, 2H), 1.95 (br m, 2H), 2.80 (br m, 2H), 3.18 (s, 3H), 3.20 and 3.33 (q, 2H), 3.45 (s, 2H), 3.80 and 3.87 (s, 2H), 3.70 and 4.10 (m, 1H), 7.2–7.3 (m, 5H), 7.48 (m, 2H), 7.82 (m, 2H); MS: 415.

Method 7

1-Phenylmethyl-4-ethylaminopiperidine dihydrochloride

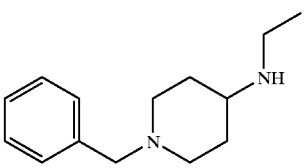

To a solution of 1-phenylmethyl-4-piperidone (25.0 g, 132 mmol) in THF (250 mL) was added ethylamine hydrochloride (12.0 g, 147 mmol) and methanol (50 mL) and the resulting mixture stirred at room temperature for 10 min. Sodium triacetoxyborohydride (40 g, 189 mmol) was added portionwise and the resulting mixture stirred at room temperature for 1 h. 2M Sodium hydroxide solution (250 mL) was added and the resulting mixture extracted with diethyl ether. The organic extracts were dried (K₂CO₃) and evaporated to give 1-phenylmethyl-4-ethylaminopiperidine as an oil. This was dissolved in ethanol (500 mL) and concentrated hydrochloric acid (20 mL) was added. The resulting crystals were collected, washed with diethyl ether and dried giving the title compound as a solid (38 g); ¹H NMR (CDCl₃): 1.10 (t, 3H), 1.40 (m, 2H), 1.83 (m, 2H), 2.02 (m, 2H), 2.65 (q, 2H), 2.85 (m, 2H), 3.50 (s, 2H), 3.75 (m, 1H), 7.2–7.4 (m, 5H); MS: 219.

Method 8

N-[1-(N-Phenyl-2-ethylamino)-4-piperidinyl]-N-ethyl-4-fluorophenylacetamide

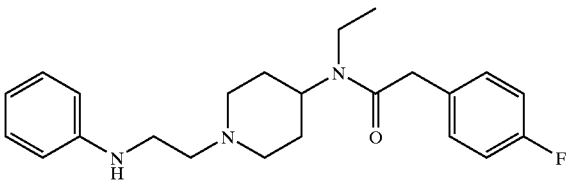

This was prepared by reacting N-4-piperidinyl-N-ethyl-4-fluorophenylacetamide with N-(2-chloroethyl)aniline hydrochloride according to the procedure used for Method 4; ¹H NMR: 1.0 and 1.5 (t, 3H), 1.3 (m, 1H) 1.5 (m, 1H), 1.7 (m, 2H), 2.0 (m, 2H), 2.4 (m, 2H), 2.9 (m, 2H), 3.1 (m, 2H), 3.2 (m, 2H), 3.6 and 3.7 (s, 2H), 4.1 (m, 1H), 5.2 (br s, 1H), 6.5 (m, 3H), 7.0 (dd, 2H), 7.1 (dd, 2H), 7.2 (m, 2H); MS: 384.

Method 9

N-4-Piperidinyl-N-ethyl-4-fluorophenylacetamide

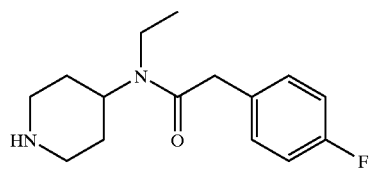

This was prepared by reacting N-(1-phenylmethyl-4-piperidinyl-N-ethyl-4-fluoro-phenylacetamide according to the procedure used for Method 5; ¹H NMR: (formic acid salt): 0.97 and 1.10 (t, 3H), 1.46 and 1.62 (m, 2H), 1.8–2.0 (m, 2H), 2.78 (m, 2H), 3.1–3.3 (m, 4H), 3.65 and 3.74 (s, 2H), 3.97 and 4.22 (m, 1H), 7.08 (m, 2H), 7.25 (m, 2H), 8.42 (s, 1H); MS: 265.

Method 10

N-(1-Phenylmethyl-4-piperidinyl-N-ethyl-4-fluorophenylacetamide

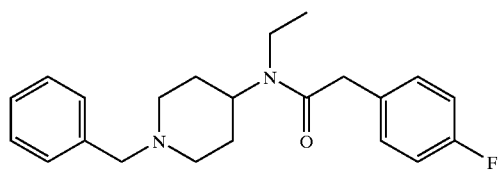

This was prepared by reacting 1-phenylmethyl-4-ethylaminopiperidine dihydrochloride with 4-fluorophenylacetic acid according to the procedure used for Method 6; $^1$H NMR (CDCl$_3$): 1.13 and 1.19 (t, 3H), 1.35 and 1.85 (m, 2H), 1.74 and 2.08 (m, 2H), 2.90 (br m, 2H), 3.30 (m, 2H), 3.46 (s, 2H), 3.66 (s, 2H), 3.55 and 4.42 (m, 1H), 7.00 (m, 2H), 7.2–7.3 (m, 7H); MS: 355.

EXAMPLE 2

The ability of compounds to inhibit the binding of RANTES or MIP-1α was assessed by an in vitro radioligand binding assay. Membranes were prepared from Chinese hamster ovary cells which expressed the recombinant human CCR5 receptor. These membranes were incubated with 0.1 nM iodinated RANTES or MIP-1α, scintillation proximity beads and various concentrations of the compounds of the invention in 96-well plates. The amount of iodinated RANTES or MIP-1α bound to the receptor was determined by scintillation counting. Competition curves were obtained for compounds and the concentration of compound which displaced 50% of bound iodinated RANTES or MIP-1α was calculated (IC$_{50}$). Certain compounds of formula (I) had an IC$_{50}$ of less than 50 μM.

SCHEME 1

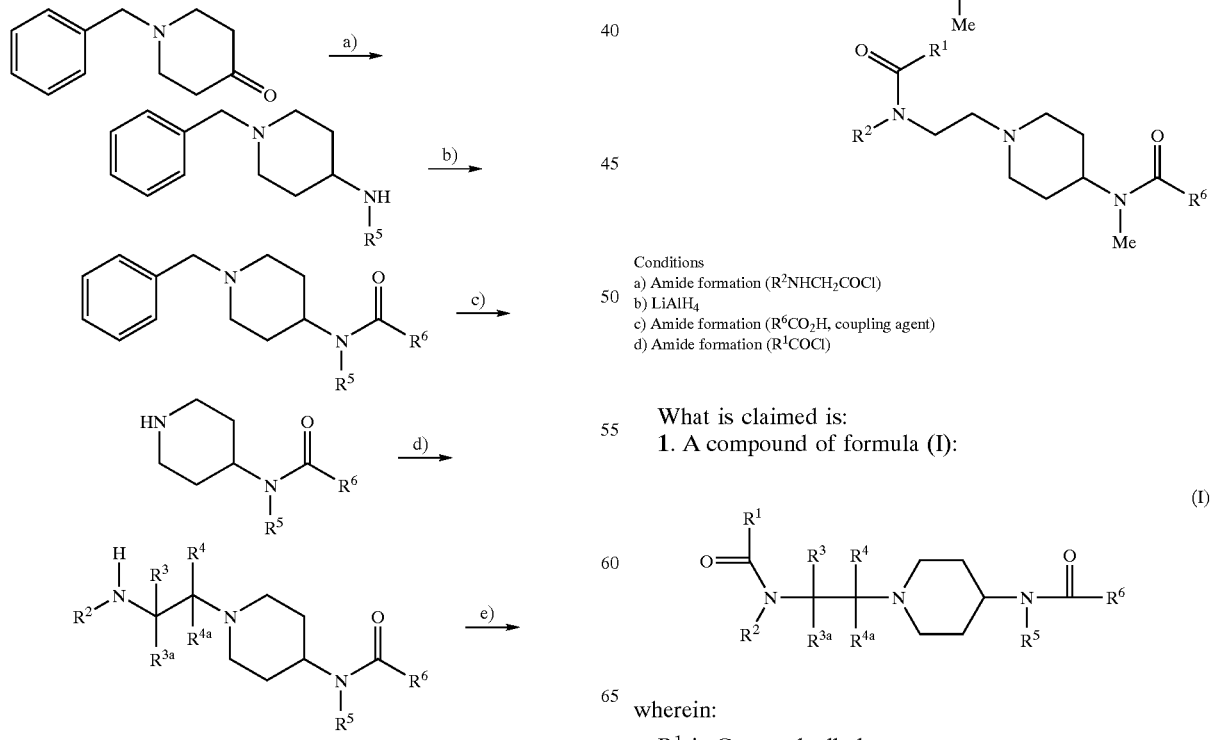

Conditions
a) Reductive amination (amine and Na(AcO)$_3$BH)
b) Amide formation (R$^6$CO$_2$H, coupling agent or R$^6$COCl)
c) H$_2$/Pd
d) alkyl halide, base
e) Amide formation (R$^1$CO$_2$H, coupling agent or R$^1$COCl)

SCHEME 2

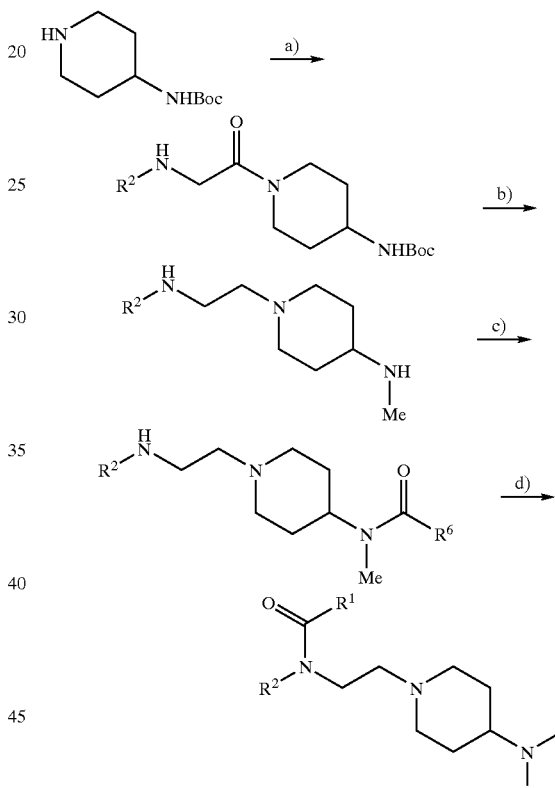

Conditions
a) Amide formation (R$^2$NHCH$_2$COCl)
b) LiAlH$_4$
c) Amide formation (R$^6$CO$_2$H, coupling agent)
d) Amide formation (R$^1$COCl)

What is claimed is:
1. A compound of formula (I):

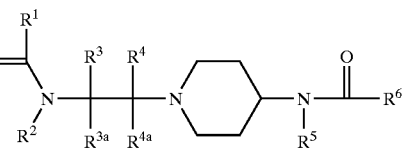

wherein:
R$^1$ is C$_{3-7}$ cycloalkyl;

$R^2$ is phenyl, heteroaryl, phenyl($C_{1-4}$ alkyl) or heteroaryl ($C_{1-4}$ alkyl);

$R^3$, $R^{3a}$, $R^4$ and $R^{4a}$ are, independently, hydrogen or $C_{1-4}$ alkyl;

$R^5$ is hydrogen, $C_{1-4}$ alkyl (optionally substituted by halogen, hydroxy, $C_{1-4}$ alkoxy, $C_{3-7}$ cycloalkyl, SH, $C_{1-4}$ alkylthio, cyano or $S(O)_q(C_{1-4}$ alkyl)), $C_{3-4}$ alkenyl, $C_{3-4}$ alkynyl or $C_{3-7}$ cycloalkyl;

$R^6$ is phenyl, heteroaryl, phenylNH, heteroarylNH, phenyl($C_{1-2}$)alkyl, heteroaryl($C_{1-2}$)alkyl, phenyl($C_{1-2}$ alkyl)NH or heteroaryl($C_{1-2}$ alkyl)NH;

wherein the phenyl and heteroaryl rings of any of the foregoing are independently optionally substituted by halo, cyano, nitro, hydroxy, $C_{1-4}$ alkyl, $C_{1-4}$ alkoxy, $S(O)_m C_{1-4}$ alkyl, $S(O)_2 NR^{11}R^{12}$, $NHS(O)_2(C_{1-4}$ alkyl), $NH_2$, $NH(C_{1-4}$ alkyl), $N(C_{1-4}$ alkyl)$_2$, $NHC(O)NH_2$, $C(O)NH_2$, $C(O)NH(C_{1-4}$ alkyl), $NHC(O)(C_{1-4}$ alkyl), $CO_2H$, $CO_2(C_{1-4}$ alkyl), $C(O)(C_{1-4}$ alkyl), $CF_3$, $CHF_2$, $CH_2F$, $CH_2CF_3$ or $OCF_3$;

$R^{11}$ and $R^{12}$ are, independently, hydrogen or $C_{1-4}$ alkyl;

m, and q are, independently, 0, 1 or 2;

or a pharmaceutically acceptable salt thereof or a solvate thereof.

2. A compound of formula (I) as claimed in claim 1 wherein $R^2$ is phenyl optionally substituted by halogen or $CF_3$.

3. A compound of formula (I) as claimed in claim 1 wherein $R^3$ and $R^{3a}$ are both hydrogen.

4. A compound of formula (I) as claimed in claim 1 wherein $R^4$ is hydrogen or methyl and $R^{4a}$ is hydrogen.

5. A compound of formula (I) as claimed in claim 1 wherein $R^5$ is hydrogen, $C_{1-4}$ alkyl, $C_{3-4}$ alkenyl, $C_{3-7}$ cycloalkyl or $C_{3-7}$ cycloalkyl($C_{1-4}$ alkyl).

6. A compound of formula (I) as claimed in claim 1 wherein $R^6$ is benzyl singly substituted by $S(O)_2(C_{1-4})$alkyl or $S(O)_2NR^9R^{10}$; wherein $R^9$ and $R^{10}$ are, independently, hydrogen or $C_{1-4}$ alkyl.

7. A process for the preparation of a compound of formula (I) as claimed in claim 1, the process comprising reacting a compound of formula (II):

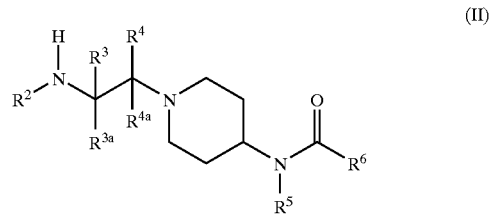

(II)

with either an acid halide of formula $R^1C(O)Cl$ in a suitable solvent, or an acid of formula $R^1CO_2H$ in the presence of a suitable coupling agent and in a suitable solvent.

8. A pharmaceutical composition which comprises a compound of the formula (I) as claimed in claim 1, or a pharmaceutically acceptable salt thereof or solvate thereof, and a pharmaceutically acceptable adjuvant, diluent or carrier.

9. A compound of formula (I) as claimed in claim 1, wherein $R^1$ is $C_{3-7}$ cycloalkyl, $R^2$ is phenyl optionally substituted by halogen or $CF_3$, $R^3$ and $R^{3a}$ are both hydrogen, $R^4$ is hydrogen or methyl and $R^{4a}$ is hydrogen, $R^5$ is hydrogen, $C_{1-4}$ alkyl, $C_{3-4}$ alkenyl, $C_{3-7}$ cycloalkyl or $C_{3-7}$ cycloalkyl($C_{1-4}$ alkyl), $R^6$ is benzyl singly substituted by $S(O)_2(C_{1-4})$alkyl or $S(O)_2NR^9R^{10}$; wherein $R^9$ and $R^{10}$ are, independently, hydrogen or $C_{1-4}$ alkyl.

10. A pharmaceutical composition as claimed in claim 8, wherein $R^1$ is $C_{3-7}$ cycloalkyl, $R^2$ is phenyl optionally substituted by halogen or $CF_3$, $R^3$ and $R^{3a}$ are both hydrogen, $R^4$ is hydrogen or methyl and $R^{4a}$ is hydrogen, $R^5$ is hydrogen, $C_{1-4}$ alkyl, $C_{3-4}$ alkenyl, $C_{3-7}$ cycloalkyl or $C_{3-7}$ cycloalkyl($C_{1-4}$ alkyl), $R^6$ is benzyl singly substituted by $S(O)_2(C_{1-4})$alkyl or $S(O)_2NR^9R^{10}$; wherein $R^9$ and $R^{10}$ are, independently, hydrogen or $C_{1-4}$ alkyl.

* * * * *